United States Patent
Edelman et al.

(10) Patent No.: US 9,011,837 B2
(45) Date of Patent: Apr. 21, 2015

(54) TISSUE-ENGINEERED ENDOTHELIAL AND EPITHELIAL IMPLANTS REPAIR MULTILAMINATE TUBULAR AIRWAY STRUCTURE

(71) Applicant: Massachusetts Institute of Technology, Cambridge, MA (US)

(72) Inventors: Elazer R. Edelman, Brookline, MA (US); Brett Zani, Quincy, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 14/098,902

(22) Filed: Dec. 6, 2013

(65) Prior Publication Data

US 2014/0099289 A1     Apr. 10, 2014

Related U.S. Application Data

(63) Continuation of application No. 13/571,494, filed on Aug. 10, 2012, now abandoned, which is a continuation of application No. 12/738,956, filed as application No. PCT/US2008/005922 on May 6, 2008, now abandoned.

(60) Provisional application No. 61/066,997, filed on Feb. 25, 2008, provisional application No. 61/002,020, filed on Nov. 6, 2007.

(51) Int. Cl.
| | | |
|---|---|---|
| *A01N 63/00* | (2006.01) | |
| *A01N 65/00* | (2009.01) | |
| *A61K 35/36* | (2006.01) | |
| *A61K 35/42* | (2006.01) | |
| *A61L 27/38* | (2006.01) | |
| *C12N 5/071* | (2010.01) | |
| *A61K 35/12* | (2006.01) | |

(52) U.S. Cl.
CPC .......... *A61K 35/36* (2013.01); *A61K 35/12* (2013.01); *A61K 35/42* (2013.01); *A61L 27/3808* (2013.01); *C12N 5/0688* (2013.01); *C12N 2500/38* (2013.01); *C12N 2501/11* (2013.01); *C12N 2501/115* (2013.01); *C12N 2501/25* (2013.01); *C12N 2501/385* (2013.01); *C12N 2501/39* (2013.01); *C12N 2501/395* (2013.01); *C12N 2501/81* (2013.01); *C12N 2502/28* (2013.01); *C12N 2533/00* (2013.01); *C12N 2533/54* (2013.01)

(58) Field of Classification Search
CPC ....... A61K 35/12; A61K 48/00; A61K 9/007; A61K 35/42; C12N 2502/28; C12N 2533/00; C12N 2533/54; C12N 5/0688
See application file for complete search history.

(56) References Cited

FOREIGN PATENT DOCUMENTS

| | | |
|---|---|---|
| WO | 96/38188 | 12/1996 |
| WO | 00/16822 | 3/2000 |
| WO | 2004/029230 | 4/2004 |
| WO | 2006/062871 | 6/2006 |
| WO | 2006/062962 | 6/2006 |
| WO | 2006/068972 | 6/2006 |
| WO | 2008/036209 | 3/2008 |
| WO | 2008/057580 | 5/2008 |
| WO | 2008/057590 | 5/2008 |

OTHER PUBLICATIONS

Centra, et al., "Culture of Bovine pulmonary artery endothelial cells on gelfoam blocks," Faseb J., 6(12):3117-3121, (1992).
Written Opinion for PCT/US2008/005922 dated Dec. 23, 2008 (6 pages).
Tournaye et al. "Testicular sperm recovery in nine 47, XXY Klinefelter patients," Human Reproduction, 1996, vol. 11, pp. 1644-1649.

*Primary Examiner* — Deborah Crouch
(74) *Attorney, Agent, or Firm* — K&L Gates LLP

(57) ABSTRACT

Endothelial implants restore vascular homeostasis after injury without reconstituting vascular architecture. Endothelial cells line the vascular epithelium and underlying vasa vasorum precluding distinction between cellular controls. Unlike blood vessels, the airway epithelium is highly differentiated and distinct from endothelial cells that line the bronchial vasa allowing investigation of the differential control tissue engineered cells may provide in airways and blood vessels. Through airway injury and cell culture models, tissue engineered implants of the bronchial epithelium and endothelium were found to promote synergistic repair of the airway through biochemical regulation of the airway microenvironment. While epithelial cells modulate local tissue composition and reaction, endothelial cells preserve the epithelium; together their relative impact was enhanced suggesting both cell types act synergistically for airway repair.

9 Claims, 7 Drawing Sheets

TISSUE-ENGINEERED ENDOTHELIAL AND EPITHELIAL IMPLANTS REPAIR MULTILAMINATE TUBULAR AIRWAY STRUCTURE

CROSS-REFERENCE TO RELATED APPLICATIONS

This application is a continuation of U.S. patent application Ser. No. 13/571,494, filed Aug. 10, 2012, which is a continuation of U.S. patent application Ser. No. 12/738,956, filed May 25, 2010, which is the U.S. national phase application under 35 U.S.C. 371 of International Patent Application No. PCT/US2008/005922, filed May 6, 2008, which claims priority to and the benefit of U.S. Provisional Patent Application No. 61/066,997, filed on Feb. 25, 2008, and U.S. Provisional Patent Application No. 61/002,020, filed on Nov. 6, 2007, the entire disclosures of each of which are incorporated by reference herein.

STATEMENT REGARDING FEDERALLY SPONSORED RESEARCH OR DEVELOPMENT

Work described herein was supported by Federal Grant No. R01, GM49039, awarded by the National Institutes of Health. The Government has certain rights to this invention.

BACKGROUND

Airways, intestines, ureters, fallopian tubes and other tubular structures possess a trilaminate form which offers structural integrity and flow modulation, as well as profound regulation of local inflammation, thrombosis and hemostasis, proliferation and remodeling. In these structures, a loose fibrous adventitia is replete with coursing arterioles, venules and neural forms, a middle muscularis layer provides control of luminal dimensions and tone, and a surface layer contains cells that biochemically regulate the wall response, and sense flow and luminal contents.

In airway disorders—such as asthma and chronic obstructive pulmonary disease (COPD)—functional imbalance is tightly associated with remodeling of airway structure. Remodeling can establish an abnormal microenvironment between the epithelium and underlying mesenchyme finally resulting in a pathophysiologic cycle of inflammatory injury and aberrant repair.

Current treatments for airway disorders and disorders of other tubular structures are limited and often have adverse consequences. Treatment options vary with age, health, and the severity of the injury or disease. One objective of the present invention is to provide methods and materials for the treatment of injured, damaged or diseased airways and other tubular structures.

BRIEF SUMMARY OF THE INVENTION

The present invention exploits the discovery that a therapeutic composition comprising cells and a biocompatible matrix, when provided locally to a tubular structure, such as an airway, can reduce or inhibit abnormal or pathological tissue remodeling typified by luminal narrowing, epithelial damage, mesenchymal cell hyperplasia, collagen deposition, hypervascularity, and inflammatory cell infiltration.

In one aspect, the invention relates to a therapeutic composition comprising a biocompatible matrix and cells in an amount sufficient to treat an injury; wherein the cells comprise bronchial epithelial cells, non-bronchial epithelial cells, non-epithelial cells or functional analogs of any one of the foregoing.

In one embodiment, the cells of the therapeutic composition comprise a mixture of bronchial epithelial cells and non-epithelial cells. In another embodiment, the non-epithelial cells of the therapeutic composition are endothelial cells. In another embodiment, the cells of the therapeutic composition comprise epithelial cells selected from the group consisting of bronchial epithelial cells; non-bronchial epithelial cells; or a mixture of bronchial epithelial cells and non-bronchial epithelial cells.

In another embodiment, the injury is an injury to a tubular structure. In another embodiment, the injury of the tubular structure is an injury to an airway. In yet another embodiment, the injury of the airway is a tracheal injury. In another embodiment, the injury of the airway is a bronchial injury. In another embodiment, the injury is as a result of disease, trauma or medical procedure.

In other embodiments, the therapeutic composition reduces an area of the injury, one or more of hypervascularity, angiogenesis, neovascularization, fibrosis, collagen deposition, inflammatory cell infiltration or necrosis, the extent of luminal narrowing or obstruction of the airway, or mesenchymal hyperplasia or hypervascularity at or nearby the site of injury. In another embodiment, the therapeutic composition enhances repair of injured epithelial cells or tissue. In another embodiment, the cells secrete an effective amount of prostaglandin $E_2$. In another embodiment, the cells reduce proliferation of lung fibroblasts. In another embodiment, the cells are autogenic, allogenic, or xenogenic.

In other embodiments, the biocompatible matrix is biodegradable, a flexible planar material and/or a flowable composition. In another embodiment, the flexible planar material is a solid polymeric support or a fibrous structure. In another embodiment, the flowable composition comprises particles, beads, gels, foams, suspensions or microcapsules or combinations of any one of the foregoing. In another embodiment, the biocompatible matrix is formed of a material selected from the group consisting of polyhydroxy acids, polyorthoesters, polyanhydrides, proteins, polysaccharides, polyphosphazenes and combinations of any one of the foregoing. In another embodiment, the biocompatible matrix is formed of a material selected from the group consisting of ethylene vinyl acetate, polyvinyl alcohol, silicone, polyurethane, non-biodegradable polyesters, polyethyleneoxide-polypropyleneoxide, tetrafluoroethylene and combinations of any one of the foregoing.

In another aspect, the invention relates to a method for treating a subject, comprising the step of providing to the subject a therapeutic composition comprising a biocompatible matrix and cells in an amount sufficient to treat an injury; wherein the cells are bronchial epithelial cells, non-bronchial epithelial cells, non-epithelial cells or functional analogs of any one of the foregoing and wherein the composition is localized at, adjacent, or in the vicinity of the injury; and further wherein the providing step is accomplished via an open-field surgical procedure or a minimally-invasive surgical procedure.

In one embodiment, the cells comprise a mixture of bronchial epithelial cells and non-epithelial cells. In another embodiment, the non-epithelial cells are endothelial cells. In another embodiment, the cells comprise epithelial cells selected from the group consisting of: bronchial epithelial cells; non-bronchial epithelial cells; or a mixture of bronchial epithelial cells and non-bronchial epithelial cells.

In another embodiment, the injury is an injury to a tubular structure, an airway, a tracheal injury or a bronchial injury. In another embodiment, the injury is as a result of disease, trauma or medical procedure. In other embodiments, the composition reduces the area of the injury, reduces one or more of hypervascularity, angiogenesis, neovascularization, fibrosis or necrosis, or reduces extent of luminal obstruction of the airway. In another embodiment, the composition enhances epithelial repair. In another embodiment, the composition reduces mesenchymal hyperplasia at or nearby the site of injury. In another embodiment, the composition reduces hypervascularity at or nearby the site of injury. In another embodiment, the cells secrete an effective amount of prostaglandin $E_2$. In another embodiment, the cells reduce proliferation of lung fibroblasts. In another embodiment, the cells are autogenic, allogenic, or xenogenic.

In another embodiment, the biocompatible matrix is biodegradable. In another embodiment, the biocompatible matrix is a flexible planar material or a flowable composition. In another embodiment, the flexible planar material is a solid polymeric support or a fibrous structure. In another embodiment, the flowable composition is particles, beads, gels, foams, suspensions or microcapsules or combinations thereof. In another embodiment, the biocompatible matrix is formed of a material selected from the group consisting of polyhydroxy acids, polyorthoesters, polyanhydrides, proteins, polysaccharides, potyphosphazenes and combinations thereof. In another embodiment, the biocompatible matrix is formed of a material selected from the group consisting of ethylene vinyl acetate, polyvinyl alcohol, silicone, polyurethane, non-biodegradable polyesters, polyethyleneoxide-polypropyleneoxide, tetrafluoroethylene and combinations thereof.

In another embodiment, the injury is an airway injury and the therapeutic composition reduces stridor resulting from the airway injury. In a further embodiment, the injury results from disease, trauma or medical procedure. In another embodiment, the therapeutic composition reduces angiogenesis and/or neovascularization resulting from the injury.

In another aspect, the invention relates to a method of effecting localized repair of a vascular injury, comprising the step of providing a composition comprising endothelial cells wherein the composition, when administered to a non-luminal surface of an injured vascular structure, promotes vascular functionality within the vasa vasorum in the vicinity of the injury while simultaneously promoting endothelial functionality within the luminal endothelium in the vicinity of the injury.

In another aspect, the invention relates to a method of effecting localized repair of injury to a tubular structure, comprising the step of providing a composition comprising endothelial cells and epithelial cells wherein the composition, when administered to a non-luminal surface of an injured tubular structure, promotes vascular functionality in the vicinity of the injury while simultaneously promoting epithelial functionality within the luminal epithelium in the vicinity of the injury. In one embodiment, the composition promotes vascular functionality within the vasa vasorum in the vicinity of the injury.

DETAILED DESCRIPTION OF THE INVENTION

Figure 1:
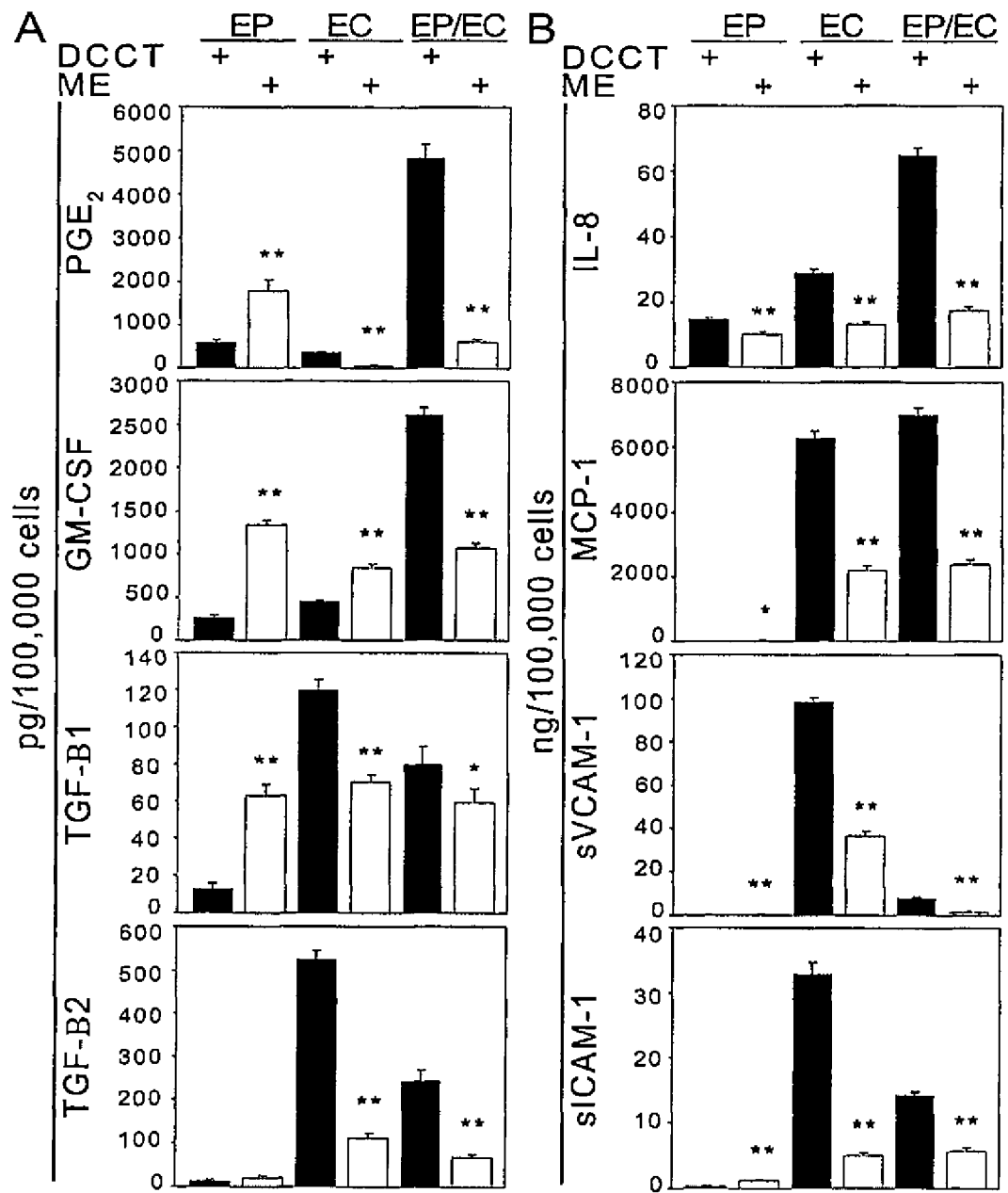
FIGS. 1A and 1B are bar graphs depicting protein secretion levels according to cell type and substrate.

Control of vascular homeostasis after injury can be regained without restoring normal and complex vascular architecture. Endothelial cells embedded within a three dimensional denatured collagen matrix secrete anti-proliferative, anti-thrombotic and anti-inflammatory agents that promote vascular repair even when such constructs are placed far from the lumen within the vascular adventitia. Lumenal inflammation, occlusive thrombosis and intimal hyperplasia can be controlled by allo- and xenogeneic matrix-embedded endothelial cells in a manner indistinct from native endothelium, and without eliciting a significant immune response. In a blood vessel, the endothelial cells of vasa vasorum and of vascular epithelium are one and the same. Thus, endothelial implants may act by recapitulating the endothelium lining as an epithelium or by adding to the regulation by perfusing vessels of the vasa vasorum which are principally comprised of endothelial cells. However, in all other physiologic tubes, such as the airway, the endothelial cells still comprise the perfusing microvasculature but a more distinct cell serves as an epithelial lining.

As explained herein, the present invention is based on the discovery that tissue engineered implants of the bronchial epithelium and endothelium promote specific and synergistic repair of the airway after injury through biochemical regulation of the airway microenvironment. Unlike blood vessels where the endothelial cell serves as both the central element of the epithelium and vasa vasorum, the airway epithelium is comprised of highly differentiated cells, including epithelial cells, that are quite distinct from the endothelial cells that line the bronchial vasorum. Thus, the present invention relates to the finding that the epithelial cells of a tissue-engineered implant limit tissue injury and mesenchymal hyperplasia, while the endothelial cells promote preservation of the epithelium and perfusion of the injured tissue. Moreover, each effect is augmented in the presence of its complimentary cell type and overall repair is increased when both cells are presented to the injured airway.

In an airway injury model described in more detail below, localized bronchial denuding injury damages epithelium, narrows bronchial lumen, and leads to mesenchymal cell hyperplasia, hypervascularity and inflammatory cell infiltration. Peribronchial tissue-engineered constructs embedded with either epithelial cells or endothelial cells limit airway injury, although better repair is obtained when both endothelial and epithelial cells are present. Endothelial cell and epithelial cell expression of Transforming Growth Factor-$\beta 2$ (TGF-$\beta 2$), Prostaglandin $E_2$ ($PGE_2$), soluble Intracellular Adhesion Molecule (sICAM-1), soluble Vascular Celt Adhesion Molecule (sVCAM-1), Interleukin-8 (IL-8), Granulocyte Macrophage-Colony Stimulating Factor (GM-CSF), Monocyte Chemoattractant Protein (MCP-1) and Transforming Growth Factor-β1 (TGF-β1) is altered by matrix embedding compared to tissue culture polystyrene, but most significantly altered when both cells were present simultaneously. Epithelial cells may provide for functional control of organ injury and fibrous response, and endothelial cells for preservation of tissue perfusion and the epithelium in particular. Together the two cells enhance functional restoration and healing suggesting that multiple cells of a tissue contribute to the differentiated biochemical function and repair of a tissue, but need not assume a fixed, ordered architectural relationship as in intact tissues to achieve these effects.

More generally, the invention relates to a cell-based therapy that can be used to treat, ameliorate, manage and/or reduce the effects of injured, damaged or diseased tubular structures, particularly multilaminate tubular structures lined by an epithelium comprised of highly differentiated cells, including epithelial cells, that are quite distinct from the endothelial cells that line the vasorum. Such tubular structures include, but are not limited to, airways, intestines, ureters and fallopian tubes. For example, the methods and compositions of the present invention may be suitable for use with fallopian tubes. Fallopian tubes are composed of three tissue layers: an inner mucosal layer comprising the epithelium, a middle muscular layer, and an outer serous layer. The methods and compositions of the present invention may also be suitable for use with tubular structures comprising more than three layers. For example, the intestine is composed of more than three layers. The intestine is made up of a mucosa, submucosa, muscularis externa and serosa. The mucosa can be further subdivided into layers, including the intestinal epithelium, lamina propria and muscularis mucosae.

The cell-based therapy can also be used in conjunction with treatments currently in use to treat injured, damaged or diseased tubular structures. The teachings presented below provide sufficient guidance to make and use the materials and methods of the present invention, and further provide sufficient guidance to identify suitable criteria and subjects for testing, measuring, and monitoring the performance of the materials and methods of the present invention.

When used in an effective amount, the cell-based therapy of the present invention, an implantable material comprising cells engrafted on, in and/or within a biocompatible matrix and having a preferred phenotype, produces factors positively associated with normal functioning of tubular structures such as airways. For example, when used in an effective amount, the cells of the implantable material, when engrafted in or within a biocompatible matrix and having a preferred phenotype, can produce quantifiable amounts of TGF-β2, PGE$_2$, sICAM-1, sVCAM-1, IL-8, GM-CSF, MCP-1, and TGF-β1.

Figure 5:
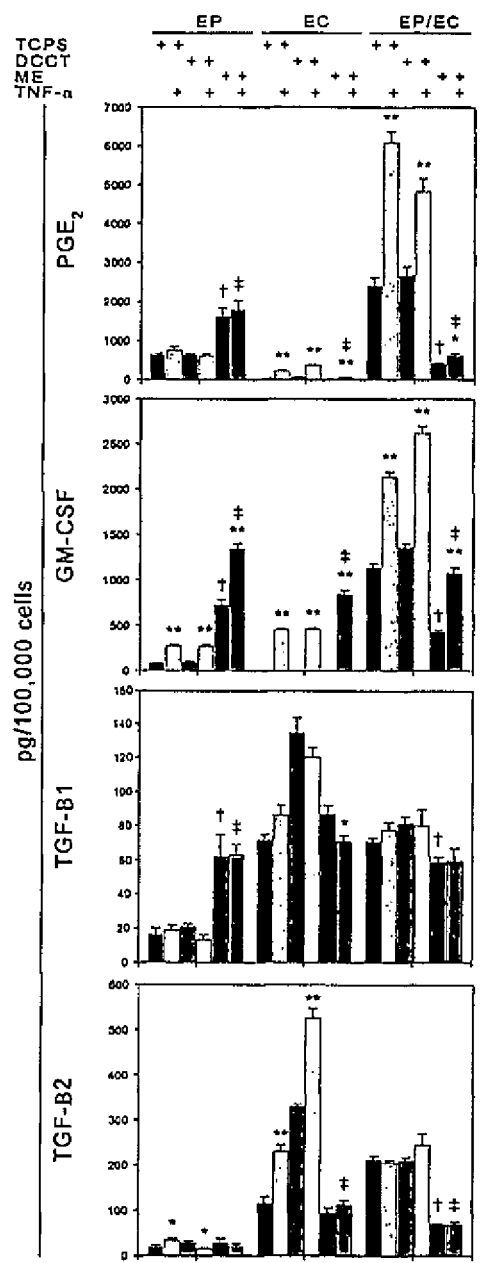
FIG. 5 is a bar graph depicting protein secretion levels of various cell types and substrates, with or without tumor necrosis factor (TNF)-$\alpha$ stimulation.
Figure 6:
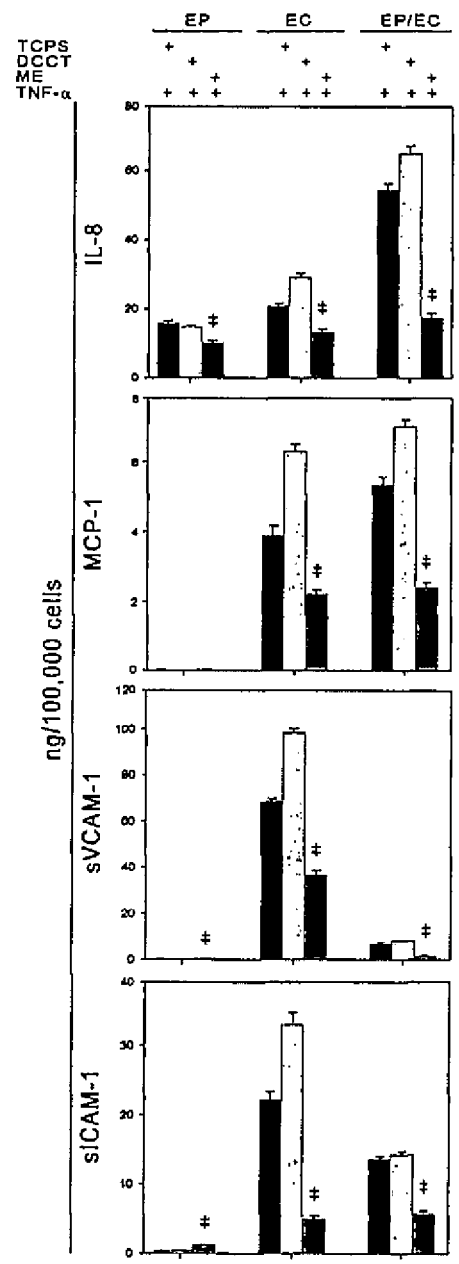
FIG. 6 is a bar graph depicting protein secretion levels of proinflammatory chemokines of various cell types and substrates.

The production of biosecretory factors involved in airway injury and repair is dependent on matrix embedding and the presence of complimentary cell type. For example, matrix-embedded endothelial cells produce lower levels of PGE$_2$ and TGF-β1 compared to endothelial cells grown on tissue culture plates. Epithelial cells embedded in a matrix produce higher levels of PGE$_2$ and TGF-β1 compared to epithelial cells grown on tissue culture plates. GM-CSF is increased in both embedded epithelial cells and endothelial cells and TGF-β2 reduced in endothelial cell constructs. In contrast, when epithelial cells and endothelial cells both occupy the matrices all molecules examined were downregulated, with or without tumor necrosis factor (TNF)-α stimulation, as seen in FIG. 1A and FIG. 5. This same is also true of the expression of proinflammatory molecules. IL-8 release is lower in all matrix-embedded cells compared to growth on TCPS and denatured collagen-coated tissue culture polystyrene, as seen in FIG. 1B and FIG. 6. MCP-1 production is reduced in embedded endothelial cells and epithelial cells/endothelial cells compared to tissue culture plate conditions. Epithelial cells expresses relatively low levels of MCP-1 compared to endothelial cells and epithelial cells/endothelial cells for all conditions. The soluble form of ICAM-1 (sICAM-1) is reduced in embedded endothelial cells and epithelial cells/endothelial cells, and increased in matrix-embedded epithelial cells compared to tissue culture plate conditions; however, epithelial cell production of sICAM-1 is relatively low compared to endothelial cells and epithelial cells/endothelial cells. Release of the soluble form of VCAM-1 (sVCAM-1) is decreased in embedded endothelial cells and epithelial cells/endothelial cells compared to tissue culture plate conditions, while epithelial cells release is higher. Similar to epithelial cells expression of sICAM-1, epithelial cells expression of sVCAM-1 is relatively low compared to endothelial cells and epithelial cells/endothelial cells for all conditions.

Accordingly, administration of an effective amount of the implantable material of the present invention can be used to treat, ameliorate, manage and/or reduce the effects of injured, damaged or diseased airways or other multilaminate tubular structures by providing a targeted supply of therapeutic factors in vivo in an amount sufficient to induce and/or maintain tissue homeostasis and reduce tissue remodeling.

Implantable Material

General Considerations:

The implantable material of the present invention comprises cells engrafted on, in and/or within a biocompatible matrix. Engrafted means securely attached via cell to cell and/or cell to matrix interactions such that the cells meet the functional or phenotypical criteria set forth herein and withstand the rigors of the preparatory manipulations disclosed herein. As explained elsewhere herein, an operative embodiment of implantable material comprises a population of cells associated with a supporting substratum, preferably a differentiated cell population and/or a near-confluent, confluent or post-confluent cell population, having a preferred functionality and/or phenotype.

Complex substrate specific interactions regulate the intercellular morphology and secretion of the cells and, accordingly, also regulate the functionality and phenotype of the cells associated with the supporting substratum. Cells associated with certain preferred biocompatible matrices, contemplated herein, may grow and conform to the architecture and surface of the local struts of matrix pores with less straining as they mold to the matrix. Also, the individual cells of a population of cells associated with a matrix retain distinct morphology and secretory ability even without complete contiguity between the cells. Further, cells associated with a biocompatible matrix may not exhibit planar restraint, as compared to similar cells grown as a monolayer on a tissue culture plate.

It is understood that embodiments of implantable material likely shed cells during preparatory manipulations and/or that certain cells are not as securely attached as are other cells. All that is required is that implantable material comprises cells associated with a supporting substratum that meet the functional or phenotypical criteria set forth herein.

That is, interaction between the cells and the matrix during the various phases of the cells' growth cycle can influence the cells' phenotype, with the preferred inhibitory phenotype described elsewhere herein correlating with quiescent cells (i.e., cells which are not in an exponential growth cycle). As explained elsewhere herein, it is understood that, while a quiescent cell typifies a population of cells which are near-confluent, confluent or post-confluent, the inhibitory phenotype associated with such a cell can be replicated by manipulating or influencing the interaction between a cell and a matrix so as to render a cell quiescent-like.

The implantable material of the present invention was developed on the principals of tissue engineering and represents a novel approach to addressing the above-described clinical needs. The implantable material of the present invention is unique in that the viable cells engrafted on, in and/or within the biocompatible matrix are able to supply to the airway or other tubular structure multiple cell-based products in physiological proportions under physiological feed-back control. As described elsewhere herein, the cells suitable for use with the implantable material include endothelial, endothelial-like, epithelial, epithelial-like cells, analogs thereof or co-cultures of any of the foregoing. Local delivery of multiple compounds by these cells in a physiologically-dynamic dosing provide more effective regulation of the processes responsible for maintaining functional airways or other tubular structures and diminishing the clinical sequel associated with injury, damage or disease to these structures.

The implantable material of the present invention, when wrapped, deposited or otherwise contacted with the surface of a injured, damaged or diseased airway or other tubular structure serves to reestablish homeostasis. That is, the implantable material of the present invention can provide an environment that mimics supportive physiology and is conducive to manage and/or promote healing at a site of airway injury, damage or disease.

For purposes of the present invention, contacting means directly or indirectly interacting with an exterior surface of an airway structure or other tubular structure, as defined elsewhere herein. In the case of certain preferred embodiments, actual physical contact is not required for effectiveness. In other embodiments, actual physical contact is preferred. All that is required to practice the present invention is exterior deposition of an implantable material at, adjacent to or in the vicinity of an injured, diseased or damaged site in an amount effective to treat the injured or diseased site. In the case of certain diseases or injuries, a diseased or injured site can clinically manifest on an interior surface. In the case of other diseases or injuries, a diseased or injured site can clinically manifest on an exterior surface of the structure. In some diseases or injuries, a diseased or injured site can clinically manifest on both an interior surface and an exterior surface of the structure or on an intermediate or adventitial layer of the structure. The present invention is effective to treat any of the foregoing clinical manifestations.

For example, endothelial cells can release a wide variety of agents that in combination can inhibit or mitigate adverse physiological conditions associated with acute complications due to injury, damage or disease to airways or other tubular structures. As exemplified herein, a composition and method of use that recapitulates normal physiology and dosing is useful to treat and manage airway healing. Typically, treatment includes placing the implantable material of the present invention at, adjacent to or in the vicinity of the injured, damaged or diseased airway. When wrapped, wrapped around, deposited, or otherwise contacting a airway structure, the cells of the implantable material can provide growth regulatory compounds to the airway structure, for example within the trachea or bronchi. It is contemplated that, while outside the airway structure, the implantable material of the present invention comprising a biocompatible matrix or particle with engrafted cells provides a continuous supply of multiple regulatory and therapeutic compounds from the engrafted cells to the airway structure.

Cell Source:

As described herein, the implantable material of the present invention comprises cells. Cells can be allogeneic, xenogeneic or autologous. In certain embodiments, a source of living cells can be derived from a suitable donor. In certain other embodiments, a source of cells can be derived from a cadaver or from a cell bank.

As stated above, suitable cells can be obtained from a variety of tissue types and cell types. In certain preferred embodiments, cells used in the implantable material are isolated from cadaver donors. In a preferred embodiment, human bronchial epithelial cells are isolated from the bronchi of a human donor. In another embodiment, human aortic endothelial cells are isolated from the aorta of a human donor. In yet another embodiment, porcine aortic endothelial cells are isolated from normal porcine aorta by a similar procedure. Each lot of cells can be derived from a single donor or from multiple donors, tested extensively for endothelial cell viability, purity, biological function, the presence of mycoplasma, bacteria, fungi, yeast, known human pathogens and other adventitious agents. The cells are further expanded, characterized and cryopreserved to form a working cell bank at the third to sixth passage using well-known techniques for later expansion in culture and for subsequent formulation in biocompatible implantable material.

In one currently preferred embodiment, cells are epithelial cells. In a more preferred embodiment, such epithelial cells are obtained from tissue comprising an airway structure. As exemplified below, one type of epithelial cell derived from an airway structure suitable for use is an bronchial epithelial cell. Another type of epithelial cell derived from an airway tissue is a tracheal epithelial cell. In a particularly preferred embodiment, cells are human bronchial epithelial cells.

In another currently preferred embodiment, suitable epithelial cells can be obtained from a tissue that is not part of an airway structure, also referred to herein as "non-airway tissue." Non-airway tissue can be derived from any anatomical structure or can be derived from any non-airway tissue or organ. Non-airway tissue can be derived from any tissue type of any anatomical structure. Exemplary anatomical structures include structures of the vascular system, the renal system, the reproductive system, the genitourinary system, the gastrointestinal system, and the ventricular system of the brain and spinal cord.

In another embodiment, epithelial cells can be derived from epithelial progenitor cells or stem cells. In still another embodiment, epithelial cells can be derived from progenitor cells or stem cells generally. In other preferred embodiments, cells can be epithelial cells that are allogeneic, xenogeneic or autologous and can be derived from any tissue or organ. Cells can be selected on the basis of their tissue source and/or their immunogenicity. The present invention also contemplates any of the foregoing which are genetically altered, modified or engineered. For example, cells may be genetically modified to overexpress or underexpress molecules involved in tissue repair, such as airway repair. Exemplary molecules to be over- or underexpressed include TGF-$\beta$2, PGE$_2$, sICAM-1, sVCAM-1, IL-8, GM-CSF, MCP-1, and TGF-$\beta$1. Cells may also be non-epithelial cells that exhibit at least some of the features of cells suitable for use with the present invention as defined elsewhere herein.

In one embodiment, suitable endothelial cells can be obtained from vascular tissue, preferably but not limited to arterial tissue, aortic endothelial cells, umbilical cord vein endothelial cells, coronary artery endothelial cells, saphenous vein endothelial cells, pulmonary artery endothelial cells, and iliac artery endothelial cells. Endothelial cells can be obtained from non-vascular tissue, progenitor cells or stem cells or from endothelial progenitor cells or stem cells. Endothelial cells can be derived from any tissue type of any anatomical structure. Exemplary anatomical structures include structures of the vascular system, the renal system, the reproductive system, the genitourinary system, the gastrointestinal system, and the ventricular system of the brain and spinal cord. Endothelial cells suitable for use in the present invention can be analogs of any of the foregoing or any other desired cell type or combination of cell types.

In a further embodiment, two or more types of cells are co-cultured to prepare the present composition. The first cell type can include, for example, any of the aforementioned cells such as epithelial cells or epithelial-like cells, endothelial cells, endothelial-like cells, analogs of any of the foregoing, or a combination of desired cell types suitable to create an environment conducive to growth of the second cell type. The second cell type may include, for example, epithelial cells, epithelial-like cells, endothelial cells, and endothelial-like cells. It is contemplated that the first and second cell types can be introduced step wise, or as a single mixture. Alternatively, a first cell can be introduced into the biocompatible implantable material and cultured until confluent. Once the first cell type has reached confluence, a second cell type is seeded on top of the first confluent cell type in, on or within the biocompatible matrix and cultured until both the first cell type and second cell type have reached confluence. It is also contemplated that cell density can be modified to alter the ratio of the first cell type to the second cell type.

To prevent over-proliferation of a cell type prone to excessive proliferation, the culture procedure and timing can be modified. For example, following confluence of the first cell type, the culture can be coated with an attachment factor suitable for the second cell type prior to introduction of the second cell type. Exemplary attachment factors include coating the culture with gelatin to improve attachment of endothelial cells. According to another embodiment, heparin can be added to the culture media during culture of the second cell type to reduce the proliferation of the first cell type and to optimize the desired first cell type to second cell type ratio.

All that is required of the cells of the present composition is that they exhibit one or more preferred phenotypes or functional properties. As described earlier herein, the present invention is based on the discovery that a cell having a readily identifiable phenotype when associated with a preferred matrix (described elsewhere herein) can facilitate, restore and/or otherwise modulate cell physiology and/or homeostasis associated with the treatment of disorders of the airway and/or other tubular structures generally.

For purposes of the present invention, one such preferred, readily identifiable phenotype typical of cells of the present invention is an ability to alter angiogenesis as measured by the in vitro tube formation assay described below. In certain preferred embodiments, the implantable material can be used for the purposes described herein when embedded epithelial cells are capable of reducing tube formation by at least about 10%-45% compared to acelluar controls. In another preferred embodiment; the implantable material can be used for the purposes described herein when embedded co-cultured epithelial cells and endothelial cells are capable of reducing tube formation by at least about 10% compared to acelluar controls.

One other readily identifiable phenotype exhibited by cells of the present composition is that they are able to control fibroblast proliferation and/or migration. Fibroblast activity can be determined using an in vitro fibroblast proliferation assay, described below. In certain preferred embodiments, the implantable material can be used for the purposes described herein when embedded epithelial cells are capable of reducing fibroblast growth by at least about 10%-15% compared to acelluar controls. In another preferred embodiment, the implantable material can be used for the purposes described herein when embedded co-cultured epithelial cells and endothelial cells are capable of reducing fibroblast growth by at least about 10% compared to acelluar controls.

In a typical operative embodiment of the present invention, cells need not exhibit more than one of the foregoing phenotypes. In certain embodiments, cells can exhibit more than one of the foregoing phenotypes.

While the foregoing phenotypes each typify a functional epithelial cell, endothelial cell or combination of epithelial and endothelial cells; non-epithelial cells or non-endothelial cells exhibiting such a phenotype(s) are considered epithelial-like or endothelial-like, respectively, for purposes of the present invention and thus suitable for use with the present invention. Cells that are epithelial-like are also referred to herein as functional analogs of epithelial cells; or functional mimics of epithelial cells. Cells that are endothelial-like are also referred to herein as functional analogs of endothelial cells; or functional mimics of endothelial cells. Thus, by way of example only, cells suitable for use with the materials and methods disclosed herein also include stem cells or progenitor cells that give rise to epithelial-like cells or endothelial-like cells; cells that are non-epithelial cells or non-endothelial cells in origin yet perform functionally like an epithelial cell or an endothelial cell, respectively, using the parameters set forth herein; cells of any origin which are engineered or otherwise modified to have epithelial-like or endothelial-like functionality using the parameters set forth herein.

Typically, cells of the present invention exhibit one or more of the aforementioned functionalities and/or phenotypes when present and associated with a supporting substratum, such as the biocompatible matrices described herein. It is understood that individual cells attached to a matrix and/or interacting with a specific supporting substratum exhibit an altered expression of functional molecules, resulting in a preferred functionality or phenotype when the cells are associated with a matrix or supporting substratum that is absent when the cells are not associated with a supporting substratum.

According to one embodiment, the cells exhibit a preferred phenotype when the basal layer of the cell is associated with a supporting substratum. According to another embodiment, the cells exhibit a preferred phenotype when present in confluent, near confluent or post-confluent populations. As will be appreciated by one of ordinary skill in the art, populations of cells, for example, substrate adherent cells, and confluent, near confluent and post-confluent populations of cells, are identifiable readily by a variety of techniques, the most common and widely accepted of which is direct microscopic examination. Others include evaluation of cell number per surface area using standard cell counting techniques such as but not limited to a hemacytometer or coulter counter.

Additionally, for purposes of the present invention, endothelial-like cells include but are not limited to cells which emulate or mimic functionally and phenotypically the preferred populations of cells set forth herein, including, for example, differentiated endothelial cells and confluent, near confluent or post-confluent endothelial cells, as measured by the parameters set forth herein.

Thus, using the detailed description and guidance set forth below, the practitioner of ordinary skill in the art will appreciate how to make, use, test and identify operative embodiments of the implantable material disclosed herein. That is, the teachings provided herein disclose all that is necessary to make and use the present invention's implantable materials. And further, the teachings provided herein disclose all that is necessary to identify, make and use operatively equivalent cell-containing compositions. At bottom, all that is required is that equivalent cell-containing compositions are effective to treat, manage, modulate and/or ameliorate an airway or other tubular structure in accordance with the methods disclosed herein. As will be appreciated by the skilled practitioner, equivalent embodiments of the present composition can be identified using only routine experimentation together with the teachings provided herein.

In certain preferred embodiments, endothelial cells used in the implantable material of the present invention are isolated from the aorta of human cadaver donors. Each lot of cells is derived from a single donor or from multiple donors, tested extensively for endothelial cell purity, biological function, the presence of bacteria, fungi, known human pathogens and other adventitious agents. The cells are cryopreserved and banked using well-known techniques for later expansion in culture for subsequent formulation in biocompatible implantable materials.

Biocompatible Matrix:

According to the present invention, the implantable material comprises a biocompatible matrix. The matrix is permissive for cell growth and attachment to, on or within the matrix. The matrix is flexible and conformable. The matrix can be a solid, a semi-solid or flowable porous composition. For purposes of the present invention, flowable composition means a composition susceptible to administration using an injection or injection-type delivery device such as, but not limited to, a needle, a syringe or a catheter. Other delivery devices which employ extrusion, ejection or expulsion are also contemplated herein. Porous matrices are preferred. The matrix also can be in the form of a flexible planar form. The matrix also can be in the form of a gel, a foam, a suspension, a particle, a microcarrier, a microcapsule, or a fibrous structure. A preferred flowable composition is shape-retaining. A currently preferred matrix has a particulate form. The biocompatible matrix can comprise particles and/or microcarriers and the particles and/or microcarriers can further comprise gelatin, collagen, fibronectin, fibrin, laminin or an attachment peptide. One exemplary attachment peptide is a peptide of sequence arginine-glycine-aspartate (RGD).

The matrix, when implanted on a surface of an airway structure, can reside at the implantation site for at least about 7-90 days, preferably about at least 7-14 days, more preferably about at least 14-28 days, most preferably about at least 28-90 days before it bioerodes.

One preferred matrix is Gelfoam® (Pfizer, Inc., New York, N.Y.), an absorbable gelatin sponge (hereinafter "Gelfoam matrix"). Another preferred matrix is Surgifoam® (Johnson & Johnson, New Brunswick, N.J.), also an absorbable gelatin sponge. Gelfoam and Surgifoam matrices are porous and flexible surgical sponges prepared from a specially treated, purified porcine dermal gelatin solution.

According to another embodiment, the biocompatible matrix material can be a modified matrix material. Modifications to the matrix material can be selected to optimize and/or to control function of the cells, including the cells' phenotype (e.g., the inhibitory phenotype) as described above, when the cells are associated with the matrix. According to one embodiment, modifications to the matrix material include coating the matrix with attachment factors or adhesion peptides that enhance the ability of the cells to control fibroblast proliferation and/or angiogenesis, or to alter the production of biosecretory factors associated with airway healing, such as TGF-β2, PGE$_2$, sICAM-1, sVCAM-1, IL-8, GM-CSF, MCP-1, and TGF-β1.

According to another embodiment, the matrix is a matrix other than Gelfoam. Additional exemplary matrix materials include, for example, fibrin gel, alginate, gelatin bead microcarriers, polystyrene sodium sulfonate microcarriers, collagen coated dextran microcarriers, PLA/PGA and pHEMA/MMA copolymers (with polymer ratios ranging from 1-100% for each copolymer). According to one embodiment, a synthetic matrix material, for example, PLA/PGA, is treated with NaOH to increase the hydrophilicity of the material and, therefore, the ability of the cells to attach to the material. According to a preferred embodiment, these additional matrices are modified to include attachment factors or adhesion peptides, as recited and described above. Exemplary attachment factors include, for example, gelatin, collagen, fibronectin, fibrin gel, and covalently attached cell adhesion ligands (including for example RGD) utilizing standard aqueous carbodiimide chemistry. Additional cell adhesion ligands include peptides having cell adhesion recognition sequences, including but not limited to: RGDY, REDVY, GRGDF, GPDSGR, GRGDY and REDV.

That is, these types of modifications or alterations of a substrate influence the interaction between a cell and a matrix which, in turn, can mediate expression of the preferred inhibitory phenotype described elsewhere herein. It is contemplated that these types of modifications or alterations of a substrate can result in enhanced expression of an inhibitory phenotype; can result in prolonged or further sustained expression of an inhibitory phenotype; and/or can confer such a phenotype on a cell which otherwise in its natural state does not exhibit such a phenotype as in, for example but not limited to, an exponentially growing or non-quiescent cell. Moreover, in certain circumstances, it is preferable to prepare an implantable material of the present invention which comprises non-quiescent cells provided that the implantable material has an inhibitory phenotype in accordance with the requirements set forth elsewhere herein. As already explained, the source of cells, the origin of cells and/or types of cells useful with the present invention are not limited; all that is required is that the cells express an inhibitory phenotype.

As stated earlier, implantable material of the present invention can be a flexible planar form or a flowable composition. When in a flexible planar form, it can assume a variety of shapes and sizes, preferably a shape and size which conforms to a contoured exterior surface of an airway or other tubular structure when situated at or adjacent to or in the vicinity of an injured or diseased site.

Flowable Composition:

In certain embodiments contemplated herein, the implantable material of the present invention is a flowable composition comprising a particulate biocompatible matrix which can be in the form of a gel, a foam, a suspension, a particle, a microcarrier, a microcapsule, macroporous beads, or other flowable material. The current invention contemplates any flowable composition that can be administered with an injection-type delivery device. For example, a delivery device such as a percutaneous injection-type delivery device is suitable for this purpose as described below. The flowable composition is preferably a shape-retaining composition. Thus, an implantable material comprising cells in, on or within a flowable-type particulate matrix as contemplated herein can be formulated for use with any injectable delivery device ranging in internal diameter from about 18 gauge to about 30 gauge and capable of delivering about 50 mg of flowable composition comprising particulate material containing preferably about 1 million cells in about 1 to about 3 ml of flowable composition.

According to a currently preferred embodiment, the flowable composition comprises a biocompatible particulate matrix such as Gelfoam® particles, Gelfoam® powder, or pulverized Gelfoam® (Pfizer Inc., New York, N.Y.) (hereinafter "Gelfoam particles"), a product derived from porcine dermal gelatin. According to another embodiment, the particulate matrix is Surgifoam™ (Johnson & Johnson, New Brunswick, N.J.) particles, comprised of absorbable gelatin powder. According to another embodiment, the particulate matrix is Cytodex-3 (Amersham Biosciences, Piscataway, N.J.) microcarriers, comprised of denatured collagen coupled to a matrix of cross-linked dextran. According to a further embodiment, the particulate matrix is CultiSpher-G (Percell Biolytica AB, Astorp, Sweden) microcarrier, comprised of porcine gelatin. According to another embodiment, the particulate matrix is a macroporous material. According to one embodiment, the macroporous particulate matrix is CytoPore (Amersham Biosciences, Piscataway, N.J.) microcarrier, comprised of cross-linked cellulose which is substituted with positively charged N,N,-diethylaminoethyl groups.

According to alternative embodiments, the biocompatible implantable particulate matrix is a modified biocompatible matrix. Modifications include those described above for an implantable matrix material.

Related flowable compositions suitable for use to manage the progression of healing in airways in accordance with the present invention are disclosed in international patent application PCT/US05/43844 filed on Dec. 6, 2005, the entire contents of which are herein incorporated by reference.

Cell Growth Curve and Confluence:

In one embodiment, normal human bronchial epithelial cells cryopreserved with retinoic acid are grown in bronchial epithelial growth medium (BEGM) supplemented with 0.4% bovine pituitary extract; 0.1% hydrocortisone; 0.1% human epidermal growth factor (hEGF); 0.1% epinephrine; 0.1% transferring; 0.1% insulin; 0.1% retinoic acid; 0.1% triiodothyronine; 0.1% gentamicin, amphotericin-B (GA-1000); and 20 units/ml penicillin-streptomycin. In one embodiment, human aortic endothelial cells are grown in endothelial growth medium-2 (EGM-2) supplemented with 10% fetal bovine serum (FBS); 0.4% hEGF; 0.04% Hydrocortisone; 0.1% R3-insulin-like growth factor-1; 0.1% vascular endothelial growth factor; 0.1% humanfibroblast growth factor-B (hFGF-B); 0.1% Ascorbic Acid; 0.1% Heparin; 0.1% GA-1000; and 20 units/ml penicillin-streptomycin. In one embodiment, epithelial cells and endothelial cells are co-cultured in a 1:1 mixture of BEGM:EGM-2.

Figure 4:
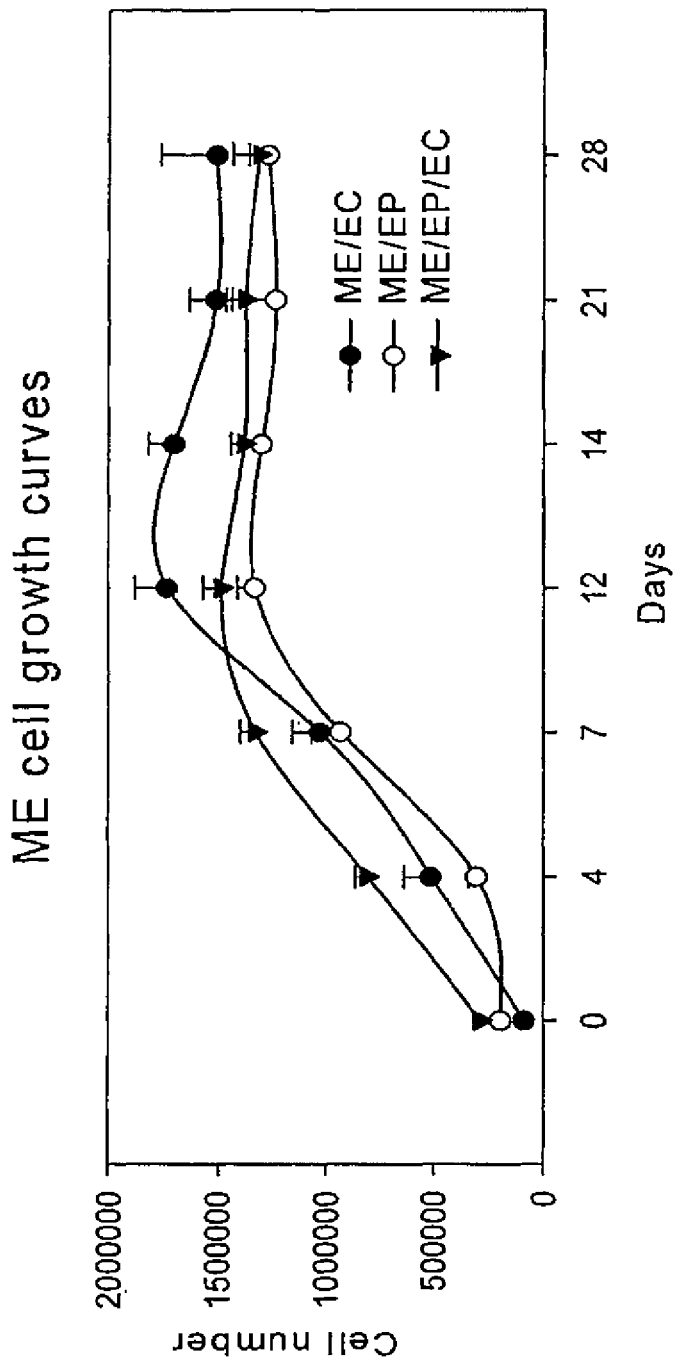
FIG. 4 is a cell growth curve depicting the number over time of epithelial cells, endothelial cells, and co-cultures of epithelial cells.

As shown in FIG. 4, epithelial cells and endothelial cells ($2 \times 10^5$ and $9 \times 10^4$ cells/matrix) grown alone or in co-culture exhibit identical growth kinetics when embedded in a biocompatible matrix. Cells reach peaked density (mean SE) at 12-14 d. To obtain similar growth kinetics over 28 days, cells are seeded in denatured collagen matrices ($2.5 \times 1.0 \times 0.3$ cm$^3$), one example of a biocompatible matrix, with initial seedings of $2 \times 10^5$ epithelial cells or $0.9 \times 10^5$ endothelial cells. Cells reach a peaked density between 12-14 d; thereafter cell numbers remain fairly constant between days 15 and 28. Cell viability, by trypan blue exclusion, averaged 91.9±0.47% for embedded epithelial cells, 92.6±0.33% for embedded endothelial cells, and 91.2±0.19% for embedded co-cultures of epithelial cells and endothelial cells over a 28-day culture period.

Preparation of Implantable Material:

In one embodiment, sheets of biocompatible matrix are cut into blocks measuring $1.5 \times 1.0 \times 0.3$ to $3.5 \times 1.0 \times 0.3$ cm$^3$. Matrices are then hydrated in bronchial epithelial growth medium (BEGM) and/or endothelial growth medium (EGM-2) for at least 30 minutes, depending on the cell type(s) to be seeded. Immediately before seeding, matrices are placed horizontally on tissue culture plates with no liquid. endothelial cells ($0.9 \times 10^5$) and/or epithelial cells ($2 \times 10^5$) are then concentrated to 100 μl and added to the surface of the matrices and incubated for 3 hours (5% $CO_2$, 37° C.). Matrices are then transferred to freestanding 15 ml polypropylene tubes containing 10 ml of EGM-2 and/or BEGM. Under standard culture conditions, cells are allowed to invade the blocks, lining the interstices of the matrices for up to 2 weeks. Cell viability was determined by trypan blue exclusion.

Evaluation of Functionality and Phenotype:

To evaluate the morphology of cells embedded in a matrix, endothelial cells, epithelial cells and co-cultures of epithelial cells and endothelial cells are grown in matrices for 12 days then scanning electron micrographs are obtained for each cell type. In preparation for image capture, the matrix embedded cells are washed once in warm PBS and fixed overnight at 4° C. with 3% glutaraldehyde. The matrices are then washed twice with PBS for 10 minutes. A 2 mm biopsy punch is used to cut cores from the middle of the matrices. The cores are washed 4 times with ultrapure water for 5 minutes. Cores are then stained for 30 minutes with a 0.5% uranyl acetate solution, followed by four washes with ultrapure water for 5 minutes. Individual cores are placed in Quantomix™ QX-102 capsules (Quantomix Ltd.). Sealed capsules are placed on the specimen stage to be viewed in the wet state with a S4300 SE-N (Hitachi High Technology) variable pressure scanning electron microscope equipped with a Schottky emitter. Imaging is performed using a backscatter detector with emission energy of 15 kV and emission current of 90-100 mA at a working distance of 9.8-9.9 mm.

When normal human bronchial epithelial and human aortic endothelial cells are grown to confluence on tissue culture polystyrene, the morphology of endothelial cells and epithelial cells is distinct. Epithelial cells exhibit a tight cobblestone appearance, while endothelial cells appear as smaller, cuboidal basal cells interspersed with larger, squamous mucous cells. Cell growth on denatured collagen-coated tissue culture polystyrene is identical to growth on tissue culture polystyrene alone. As on tissue culture polystyrene, the morphology of matrix-embedded endothelial cells and matrix-embedded epithelial cells is distinct. Endothelial cells and epithelial cells attain planar confluence on tissue culture polystyrene but show less constrained forms in matrices. Matrix embedding enables cell growth with less strained conformational molding to substratum, without imposing planar restraint, and retention of distinct morphology and secretory ability even without complete contiguity. Embedded endothelial cells retain a cobblestone appearance, and epithelial cells appear in their native cuboidal basal and squamous mucosal forms. Visual observation of co-cultures of epithelial cells and endothelial cells on tissue culture polystyrene shows that cells remain in isolated single cell colonies separated by an extracellular matrix barrier, while on matrices the cell types are interspersed with no apparent interceding physical barrier. Matrix embedding allows cells to attain a conformation not limited to planar restrictions imposed by tissue culture polystyrene or the distinct isolation of cell types and interposing barrier. Embedded cells conform to the architecture and surface of the local struts of matrix pores in a lesser strained configuration.

For purposes of the invention described herein, the implantable material is further tested for indicia of functionality and phenotype prior to implantation. To evaluate the presence and/or amount of airway-repair and injury-specific molecules, endothelial cells and/or epithelial cells are grown to confluence. The same fresh medium (BEGM, EGM-2, or BEGM:EGM-2, 1:1) is then added with or without TNF-$\alpha$, (10 ng/ml, Sigma) for all conditions. Cells are trypsinized from tissue culture polystyrene and denatured collagen-coated tissue culture polystyrene and counted with a cell counter (Coulter Counter). Cells in matrices are detached by collagenase type I (1 mg/ml, Worthington) digestion and counted using a hemocytometer. Release of TGF-$\beta$2 (R&D Systems), $PGE_2$ (Cayman Chemical), sICAM-1, sVCAM-1, IL-8, GM-CSF, MCP-1 and TGF-$\beta$1 (Invitrogen) is measured using commercially available ELISA kits according to the manufacturers' instructions. Fresh medium is incubated without cells for 24 hours and a baseline level for each soluble factor is measured at the same time as medium with cells. The baseline levels are then subtracted from the experimental raw data to obtain the cellular expression of each soluble factor. The results for each soluble factor are then normalized by cell number and expressed in either picograms or nanograms per $10^5$ cells. TGF-$\beta$2, $PGE_2$, sICAM-1, sVCAM-1, IL-8, GM-CSF, MCP-1 and TGF-$\beta$1 levels can also be quantified using monoclonal or polyclonal antibodies, preferably polyclonal. Control collection media can also be quantitated using an ELISA assay or other means, and the samples corrected appropriately for TGF-$\beta$2, $PGE_2$, sICAM-1, sVCAM-1, IL-8, GM-CSF, MCP-1 and TGF-$\beta$1 levels present in control media.

Epithelial cells and endothelial cells cultured separately or together secrete different patterns of molecules known to play a role in airway injury and repair when they are grown on tissue culture polystyrene as compared to denatured collagen-coated tissue culture polystyrene, and these cellular secretion levels are modulated further when these cells are matrix embedded (FIGS. 1, 5, 6). All molecules examined to date are downregulated in co-embedded epithelial cells and endothelial cells, with or without TNF-$\alpha$ stimulation. While epithelial cells embedded alone express higher levels of $PGE_2$, GM-CSF and TGF-$\beta$1, embedded endothelial cells secrete lower levels of $PGE_2$, TGF-$\beta$1 and TGF-$\beta$2 compared to cells on tissue culture polystyrene and denatured collagen-coated tissue culture polystyrene. The diverse expression patterns among epithelial cells, endothelial cells and epithelial cells/endothelial cells grown on tissue culture polystyrene, denatured collagen-coated tissue culture polystyrene or in matrices may arise from complex cellular, biochemical and substrate specific interactions regulating cellular secretion.

The peri-bronchial infiltration of inflammatory cells in xenogeneic embedded endothelial cell and epithelial cell implants is moderate. In addition, the expression of pro-inflammatory molecules IL-8, MCP-1, sICAM-1 and sVCAM-1 is reduced by embedding endothelial cells and epithelial cells together. Embedded epithelial cells alone produce lower levels of IL-8 compared to epithelial cells grown on tissue culture polystyrene or denatured collagen-coated tissue culture polystyrene, but produce more sICAM-1 and sVCAM-1; all of these levels are relatively low compared to that produced by endothelial cells are grown alone, or by co-cultured epithelial cells and endothelial cells. One novel feature of the present invention is that embedding a cell type other than endothelial cells alters expression levels of proinflammatory molecules. Without wishing to be bound by the theory, these results suggest that altered molecule expression and reduced cell immunogenicity of embedded cells arise from cell attachment and/or the interaction of the cells with a specific supporting substratum. The results corroborate earlier data that show that cells embedded in a matrix behave differently than cells not embedded in a matrix.

For cultured epithelial cells and co-cultured epithelial and endothelial cells, conditioned media may be collected during the culture period to ascertain levels of Prostaglandin $E_2$ ($PGE_2$), Granulocyte Macrophage-Colony Stimulating Factor (GM-CSF), TGF-$\beta_1$, and TGF-$\beta_2$ produced by cultured epithelial cells and cocultured epithelial and endothelial cells. In certain preferred embodiments, the implantable material can be used for the purposes described herein when $PGE_2$ in epithelial cell conditioned media is about 0.5-2.5 ng/mL/day and preferably at least about 1.5 ng/mL/day, while $PGE_2$ produced in conditioned media by cocultured epithelial and endothelial cells is about 0.25-0.5 ng/mL/day and preferably at least about 0.4 ng/mL/day; GM-CSF in epithelial cell conditioned media is below 1.0 ng/mL/day and preferably no more than about 0.7 ng/mL/day, while GM-CSF produced in conditioned media by cocultured epithelial and endothelial cells is below 0.6 ng/mL/day and preferably no more than about 0.45 ng/mL/day; TGF-$\beta_1$ in both epithelial cell conditioned media and cocultured epithelial and endothelial conditioned media is 100-200 picog/mL/day and preferably at least about 200 picog/ml/day; TGF-$\beta_2$ in epithelial cell conditioned media is about 25-100 picog/ml/day and preferably at least about 50 picog/mL/day, while TGF-$\beta_2$ produced in conditioned media by cocultured epithelial and endothelial cells is about 150-250 picog/mL/day and preferably at least about 225 picog/ml/day.

For cultured endothelial cells, conditioned media may also be collected during the culture period to ascertain levels of heparan sulfate, transforming growth factor-$\beta_1$ (TGF-$\beta_1$), basic fibroblast growth factor (b-FGF), tissue inhibitors of matrix metalloproteinases (TIMP), and nitric oxide (NO) which are produced by the cultured endothelial cells. In certain preferred embodiments, the implantable material can be used for the purposes described herein when total cell number is at least about $2 \times 10^5$ cells/$cm^3$, preferably at least about $4 \times 10^5$ cells/$cm^3$ of implantable material; percentage of viable cells is at least about 80-90%, preferably $\geq$90%, most preferably at least about 90%; heparan sulfate in conditioned media is at least about 0.23-1.0, preferably at least about 0.5 microg/mL/day; TGF-$\beta$1 in conditioned media is at least about 200-300 picog/mL/day, preferably at least about 300 picog/ml/day; b-FGF in conditioned media is below about 200 picog/ml, preferably no more than about 400 picog/ml; TIMP-2 in conditioned media is at least about 5.0-10.0 ng/mL/day, preferably at least about 8.0 ng/mL/day; NO in conditioned media is at least about 0.5-3.0 $\mu$mol/L/day, preferably at least about 2.0 $\mu$mol/L/day.

When ready for implantation, the planar form of implantable material is supplied in final product containers, each preferably containing a 1×4×0.3 cm (1.2 $cm^3$), sterile implantable material with preferably approximately $5-8 \times 10^5$ or preferably at least about $4 \times 10^5$ cells/$cm^3$, and at least about 90% viable cells (for example, human bronchial epithelial cells and/or human aortic endothelial cells derived from a single cadaver donor) per cubic centimeter implantable material in approximately 45-60 ml, preferably about 50 ml, epithelial growth medium (for example, bronchial epithelial growth medium (BEGM)), and/or endothelial growth medium (for example, endothelial growth medium (EGM-2)). When porcine aortic endothelial cells are used, the growth medium is also EBM-2 containing no phenol red, but supplemented with 5% FBS and 50 μg/ml gentamicin.

In other preferred embodiments, the flowable composition (for example, a particulate form biocompatible matrix) is supplied in final product containers, including, for example, sealed tissue culture containers modified with filter caps or pre-loaded syringes, each preferably containing about 50-60 mg of flowable composition comprising about $7 \times 10^5$ to about $1 \times 10^6$ total endothelial cells in about 45-60 ml, preferably about 50 ml, growth medium per aliquot.

Shelf-Life of Implantable Material:

The implantable material of the present invention comprising a confluent, near-confluent or post-confluent population of cells can be maintained at room temperature in a stable and viable condition for at least two weeks. Preferably, such implantable material is maintained in about 45-60 ml, more preferably about 50 ml, of transport media with or without additional FBS or VEGF. Transport media comprises EGM-2 and/or BEGM media without phenol red. FBS can be added to the volume of transport media up to about 10% FBS, or a total concentration of about 12% FBS. However, because FBS must be removed from the implantable material prior to implantation, it is preferred to limit the amount of FBS used in the transport media to reduce the length of rinse required prior to implantation. VEGF can be added to the volume of transport media up to a concentration of about 3-4 ng/ml.

Cryopreservation of Implantable Material:

The implantable material of the present invention can be cryopreserved for storage and/or transport to the implantation site without diminishing its clinical potency or integrity upon eventual thaw. Preferably, implantable material is cryopreserved in a 15 ml cryovial (Nalgene®, Nalge Nunc Int'l, Rochester, N.Y.) in a solution of about 5 ml CryoStor CS-10 solution (BioLife Solutions, Oswego, N.Y.) containing about 10% DMSO, about 2-8% Dextran and about 20-75% FBS. Cryovials are placed in a cold iso-propanol water bath, transferred to an −80° C. freezer for 4 hours, and subsequently transferred to liquid nitrogen (−150° C. to −165° C.).

Cryopreserved aliquots of the implantable material are then slowly thawed at room temperature for about 15 minutes, followed by an additional approximately 15 minutes in a room temperature water bath. The material is then washed about 3 times in about 200-250 mL saline, lactated ringers or EBM. The three rinse procedures are conducted for about 5 minutes at room temperature. The material may then be implanted.

To determine the bioactivity of the thawed material, following the thaw and rinse procedures, the cryopreserved material is allowed to rest for about 48 hours in about 10 ml of recovery solution. For porcine endothelial cells, the recovery solution is EBM-2 supplemented with 5% FBS and 50 μg/ml gentamicin at 37° C. in 5% $CO_2$; for human endothelial cells, the recovery solution is EGM-2 with or without antibiotics; for human bronchial epithelial cells, the recovery solution is BEGM. Further post-thaw conditioning can be carried out for at least another 24 hours prior to use and/or packaging for storage or transport.

Immediately prior to implantation, the transport or cryopreservation medium is decanted and the implantable material is rinsed in about 250-500 ml sterile saline (USP). The medium in the final product contains a small amount of FBS to maintain cell viability during transport to a clinical site if necessary. The FBS has been tested extensively for the presence of bacteria, fungi and other viral agents according to Title 9 CFR: Animal and Animal Products. A rinsing procedure is employed just prior to implantation, which decreases the amount of FBS transferred preferably to between 0-60 ng per implant, but preferably no more than 1-2 μg per implant.

The total cell load per human patient will be preferably approximately $1.6-2.6 \times 10^4$ cells per kg body weight, but no less than about $2 \times 10^3$ and no more than about $2 \times 10^6$ cells per kg body weight.

Administration of Implantable Material:

The implantable material of the present invention when in a flowable composition comprises a particulate biocompatible matrix and cells, preferably endothelial cells and epithelial cells, more preferably vascular endothelial cells and bronchial epithelial cells, which are about 90% viable at a preferred density of about $0.8 \times 10^4$ cells/mg, more preferred of about $1.5 \times 10^4$ cells/mg, most preferred of about $2 \times 10^4$ cells/mg. When cultured alone, endothelial cells can produce conditioned media containing heparan sulfate at least about 0.23-1.0, preferably at least about 0.5 microg/mL/day, TGF-$\beta_1$ at at least about 200-300 picog/ml/day, preferably at least about 300 picog/ml/day, and b-FGF below about 200 picog/ml and preferably no more than about 400 picog/ml; TIMP-2 in conditioned media is at least about 5.0-10.0 ng/mL/day, preferably at least about 8.0 ng/mL day; NO in conditioned media is at least about 0.5-3.0 μmol/L/day, preferably at least about 2.0 μmol/L/day; and, display the earlier-described inhibitory phenotype. When cultured alone, epithelial cells can produce conditioned media containing $PGE_2$ at least about 0.5-2.5 ng/mL/day, preferably at least about 1.5 ng/mL/day; GM-CSF at least below about 1.0 ng/mL/day and preferably no more than about 0.7 ng/mL/day; TGF-$\beta_1$ at least about 100-200 picog/mL/day and preferably at least about 200 picog/mL/day; TGF-$\beta_2$ at least about 25-100 picog/mL/day and preferably at least about 50 picog/mL/day; and, display the earlier-described inhibitory phenotype as measured by the fibroblast proliferation assay and the tube formation assay, described below. Cocultured epithelial and endothelial cells can produce conditioned media containing $PGE_2$ at least about 0.25-0.5 ng/mL/day and preferably at least about 0.4 ng/mL/day; GM-CSF below about 0.6 ng/mL/day and preferably no more than about 0.45 ng/mL/day; TGF-$\beta_1$ at least about 100-200 picog/mL/day and preferably at least about 200 picog/ml/day; TGF-$\beta_2$ at least about 150-250 picog/mL/day and preferably at least about 225 picog/mL/day; and, display the earlier-described inhibitory phenotype.

For purposes of the present invention generally, administration of the implantable particulate material is localized to a site in the vicinity of, adjacent or at a site of disease, damage or blockage of an airway or other tubular structure. The site of deposition of the implantable material is an exterior surface of a an airway or other tubular structure. As contemplated herein, localized deposition can be accomplished as follows.

In a particularly preferred embodiment, the flowable composition is first administered percutaneously, entering the patient's body near the airway or other tubular structure and then deposited on an exterior surface of the airway or other tubular structure using a suitable needle, catheter or other suitable percutaneous delivery device. Alternatively, the flowable composition is delivered percutaneously using a needle, catheter or other suitable delivery device in conjunction with an identifying step to facilitate delivery to a desired exterior surface of the airway or other tubular structure. The identifying step can occur prior to or coincident with percutaneous delivery. The identifying step can be accomplished using physical examination, ultrasound, and/or CT scan, to name but a few. The identifying step is optionally performed and not required to practice the methods of the present invention.

Preferably, flowable composition is deposited on an exterior surface of a airway or other tubular structure, either at the site of disease or damage to be treated, or adjacent to or in the vicinity of the site of disease or damage. The composition can be deposited in a variety of locations relative to an airway or other tubular structure, for example, at the site of damage or disease, surrounding the site of damage or disease or adjacent to the site of damage or disease. According to a preferred embodiment, an adjacent site is within about 0 mm to 20 mm of the airway. In another preferred embodiment, a site is within about 21 mm to 40 mm; in yet another preferred embodiment, a site is within about 41 mm to 60 mm. In another preferred embodiment, a site is within about 61 mm to 100 mm. Alternatively, an adjacent site is any other clinician-determined adjacent location where the deposited composition is capable of exhibiting a desired effect on a airway or other tubular structure in the proximity of the site of the airway or other tubular structure.

In another embodiment, the flowable composition is delivered directly to a surgically-exposed non-luminal surface at, adjacent to or in the vicinity of an airway. In this case delivery is guided and directed by direct observation of the site. Also in this case, delivery can be aided by coincident use of an identifying step as described above. Again, the identifying step is optional.

According to another embodiment of the invention, the flexible planar form of the implantable material is delivered locally to a surgically-exposed extraluminal, non-luminal, exterior site or interior cavity at, adjacent to or in the vicinity of an airway. In one case, at least one piece of the implantable material is applied to a desired site by passing one end of the implantable material under an airway structure. The ends are then wrapped around the structure, keeping the implantable material centered. The ends overlap each other to secure the material in place. In other cases, the implantable material does not need to completely wrap around the circumference of the structure; it need only conform to and contact a surface of the structure and be implanted in an amount effective to treat a damaged or diseased site.

EXAMPLE 1

Endothelial and Epithelial Cell Implants Differentially Regulate Airway Repair

In the present study, an in vivo airway injury model was employed to understand whether injury and repair of the airway is mediated by the first line sensor—the airway epithelium—or by the endothelial cells of the perfusing vasculature. Tissue engineered implants of the bronchial epithelium and endothelium promoted specific and synergistic repair of the airway through biochemical regulation of the airway microenvironment. While epithelial cells modulate local tissue composition and reaction, endothelial cells preserve the epithelium and perfusing microvasculature; together their relative impact was enhanced suggesting both cell types together increase airway repair. From these findings it may be inferred that in vascular injury, engineered endothelial cells implants recapitulate aspects of endothelial cells from both the epithelium and the perfusing microvasculature, while airways and other tubular organs likely require distinct epithelial and endothelial implants to achieve the same degree of repair. In all of these cases healing does not require the reconstitution of architecture.

Animals and Surgical Procedure:

This study conformed to the guidelines specified in the National Institutes of Health Guide for Care and Use of Laboratory Animals and was approved by the Harvard Medical Area Standing Committee on Animals. At Day 0, twenty-nine female New Zealand white rabbits (3.5 to 4.7 kg and 6 months to 1 year old) were sedated with Acepromazine (1 mg/kg-IM), Glycopyrrolate (0.01 mg/kg-IM) and Butorphanol (0.2 mg/kg-IM). Induction was performed using Medetomidine (0.25 mg/kg-SQ), followed by a general anesthetic of Isoflorane (1-2%) and Oxygen on a pediatric non-rebreathing anesthetic system. The rabbits were started on isoflurane and oxygen as its anesthetic during the surgical procedure. Prior to intubation, a 2% Cetacaine spray was used to prevent larygnospasm. The animals were placed in the supine position on a heated operating table, and heart rate and $PO_2$ were monitored throughout the procedure. A long midline incision was made exposing the trachea. A 2 mm nylon brush inserted through an endotracheal tube was advanced and withdrawn across a defined area of the trachea ten times, inducing a localized and locatable injury of the epithelial lining. The injured site was then wrapped with matrices containing no cells, endothelial cells, epithelial cells or a co-culture of epithelial cells and endothelial cells. Injured and untreated animals served as controls. Localized nylon brush injury of rabbit tracheal epithelium was confirmed with trypan blue dye transport. (Trypan blue is excluded from deposition in the bronchial wall by an intact epithelium but only in areas of remnant epithelium after localized nylon brush injury. Areas of epithelial denudation are demarcated by dark blue infiltration.) After airway epithelial injury and implantation of biocompatible matrices, the midline incisions were sutured closed and the animals observed in separate cages during recovery. The rabbits were observed daily for respiratory distress, stridor, general health and activity. At any sign of airway obstruction, the rabbit was euthanized. At Day 9 after injury, the presence or lack of respiratory stridor was recorded. The rabbits were then sacrificed and samples removed for histological and morphological examination.

Tissue Processing and Analysis:

After removal, the tracheas were fixed in 10% formalin and sectioned into 3-mm-long segments. Multiple segments proximal to the injury, at the injury and distal to the injury were paraffin-embedded. Five-micrometer sections were obtained from the proximal, middle and distal segments and stained with hematoxylin-eosin and verHoeffs elastin stain. Photomicrographs were taken with a DC-70 digital camera (Olympus). The degree of airway injury was determined by morphometric analysis in which the lumen (L), epithelium (E), mesenchyme (M), mesenchyme injury (I), cartilage (C) and vascular (V) areas were measured in Adobe Photoshop CS3 software by an observer blinded to the treatment groups. For each trachea, all area measurements in the injured tracheal segments were represented as percent control by using the measurements of the uninjured tracheal segments proximal and distal to the injury as internal controls. The extent of mesenchyme injury was based on the combined areas of inflammation, fibrosis and necrosis with the area being normalized for the size of the entire mesenchyme area.

Pathologic changes in the airway 9 days after brush injury of the tracheal epithelial lining included lumen narrowing, epithelial damage, mesenchyme cell hyperplasia, collagen deposition, hypervascularity and infiltration of inflammatory cells, reminiscent of the pathological characteristics of airway diseases. Tissue effects were mirrored on a cellular level. Acellular implants induced modest peribronchial inflammation with more extensive tissue damage, mesenchymal hyperplasia, neovascularization and luminal narrowing. Embedded endothelial cells or epithelial cells alone reduced these effects, and optimally when both cells were present in the constructs. Extensive cell damage and airway remodeling were noted in the absence of further intervention compared to control uninjured airways and unaffected by matrices alone. Matrix-embedded cells enhanced repair in a distinct manner when alone, and synergistically when cultured together.

Figure 2:
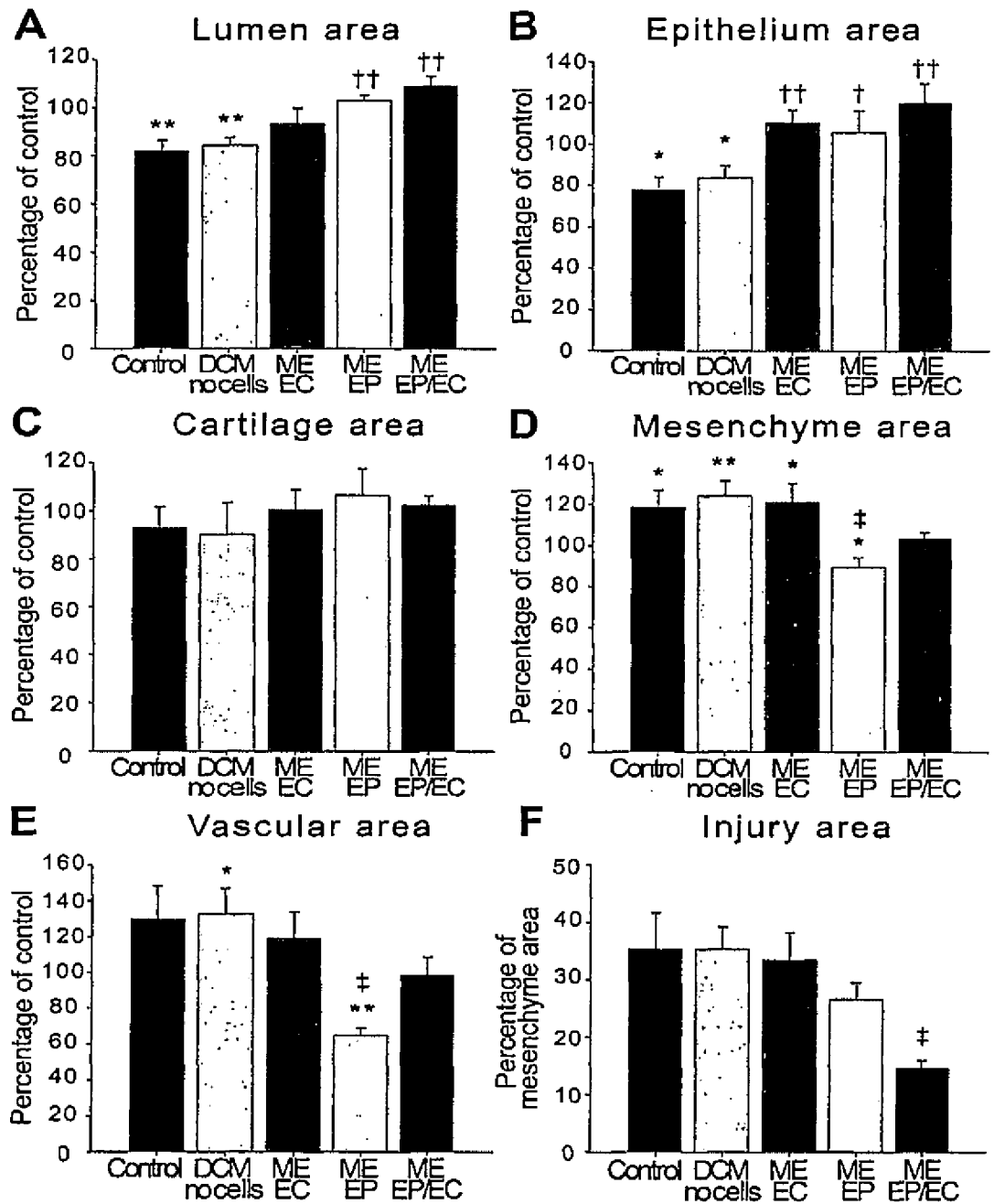
FIGS. 2A-2F are bar graphs depicting the effect of epithelial cells and endothelial cells on tracheal healing in a rabbit airway.

Luminal obstruction and airway remodeling were controlled by matrix-embedded epithelial cells, alone and with matrix-embedded endothelial cells, and to a lesser extent isolated matrix-embedded endothelial cells (FIG. 2). The area of the airway lumen was reduced with injury (−17.9±4.2%, compared to uninjured control segments). While acellular matrices had no affect on this injury, the lumen was preserved in major part by matrix-embedded endothelial cells with a 62.5±6.5% reduction in lumenal occlusion, and dilated to a degree by embedded epithelial cells (3.0±2.3%) and even greater with matrix-embedding of both cells in a co-culture together (8.9±4.0%) (FIG. 2A). Epithelial area was reduced 22.0±5.9% by injury and was unaffected by acellular implants, while best preserved in tracheas wrapped with embedded endothelial cells alone (110.5±6.1%) or with epithelial cells (120.1±9.3%), but to lesser extent with epithelial cells (105.6±10.5% (FIG. 2B). There was no difference in cartilage area among all the conditions (FIG. 2C). Mesenchymal hyperplasia was evident after injury as a 18.9±8.0% increase in thickness and made if anything subtly worse with empty matrices (124.3±7.2%). Endothelial cells implants had no effect, epithelial cell matrices reduced thickening by 40.0±1.8%, and virtually eliminated hyperplasia altogether with implants containing both endothelial cells and epithelial cells (FIG. 2D). Injured airways were hypervascular with 29.9±18.5% greater vessel density and similarly marginally worse when wrapped with acellular matrices 32.9±14.4%, marginally better with embedded endothelial cells, significantly reduced by epithelial cells (64.9±4.4%), and relatively normal in matrices with both cells (FIG. 2E). Tissue injury as a percentage of mesenchyme area was 2.4 fold reduced in tracheas wrapped with epithelial cells and endothelial cells (14.5±1.4%) compared to no implants, empty implants or implants with endothelial cells (FIG. 2F). Embedded epithelial cells had a mid-range effect with a 24.9±0.75% reduction in injury. These results indicate that while both cell types promote epithelial recovery, epithelial cells protect mesenchymal hyperplasia and prevent neovascularization. Together the two cells increase repair.

As the matrix implants degrade they allow for moderate and controlled inflammatory cell infiltration. This was evident in all sections and was no different in implants with and without cells. Similarly, tissue inflammation was identical with or without implanted matrices. The extent of fibrosis and necrosis was less in tracheas wrapped with matrices containing epithelial cells alone or co-cultured with endothelial cells. The incidence of stridor in the rabbits was recorded 9 days after brush injury. Only 1 of 6 (17%) rabbits that did not have implants exhibited signs of stridor, while stridor was presented in 5 of 7 (71%) rabbits treated with acellular devices. The peribronchial cuffing from implanted matrices may induce even greater injury as seen in other wrapped injured organs. Airflow was sufficiently restricted by the combined brush denudation from within, and acellular matrices from without, to raise the incidence of stridor more than 4 fold compared to injury alone. Embedding endothelial cells within the matrices reduced stridor 3 fold, and embedding epithelial cells or co-cultures of epithelial cells and endothelial cells eliminated stridor altogether, suggesting that matrix embedding of cells provides a functional benefit for airway repair and not simply biochemical signals.

Airway remodeling that accompanies diseases, such as asthma and chronic obstructive pulmonary disease, includes major structural and functional changes to the mesenchyme along with angiogenesis and microvascular remodeling. Larger, more abundant and dysfunctional blood vessels are formed with uncontrolled permeability, leukocyte adhesion and local inflammation. The impact of embedded epithelial cells extended into these domains as well, restricting the hypervascular mesenchymal response to injury, but to such an extent that this layer was perhaps underperfused (65% of control). Tracheobronchial segments treated with embedded endothelial cells were hyperplastic (121% of control) and hypervascular (119% of control) no different than untreated tissue. Together endothelial cells and epithelial cells however increased all indices of repair by restoring luminal and epithelium areas, inhibiting mesenchymal hyperplasia and hypervascularity, and significantly reducing the extent of tissue injury (FIG. 2).

EXAMPLE 2

Fibroblast Growth Inhibited by Matrix-Embedded Cells

Fibroblasts are essential supporting cells of the airway and of the mesenchymal hyperplastic lesion. To determine the effect of matrix-embedded cells on fibroblast proliferation, normal human lung fibroblasts (NHLF) were seeded at $5\times10^4$ cells/well and grown for 48 hours on 6-well transwell plates (Costar). Fresh medium (5 ml/well of BEGM:EGM-2, 1:1) was then added with or without 5 µM indomethacin (Sigma) and 24 mm inserts (0.4 µm membrane) with matrices (engrafted with endothelial cells, epithelial cells, or co-cultures of epithelial cells and endothelial cells) placed on top of the NHLF. After an additional 48 hours, NHLF were trypsinized and total cell number for each well was determined with a cell counter (Coulter Counter). Medium was collected and analyzed using commercially available ELISA kits.

Figure 3:
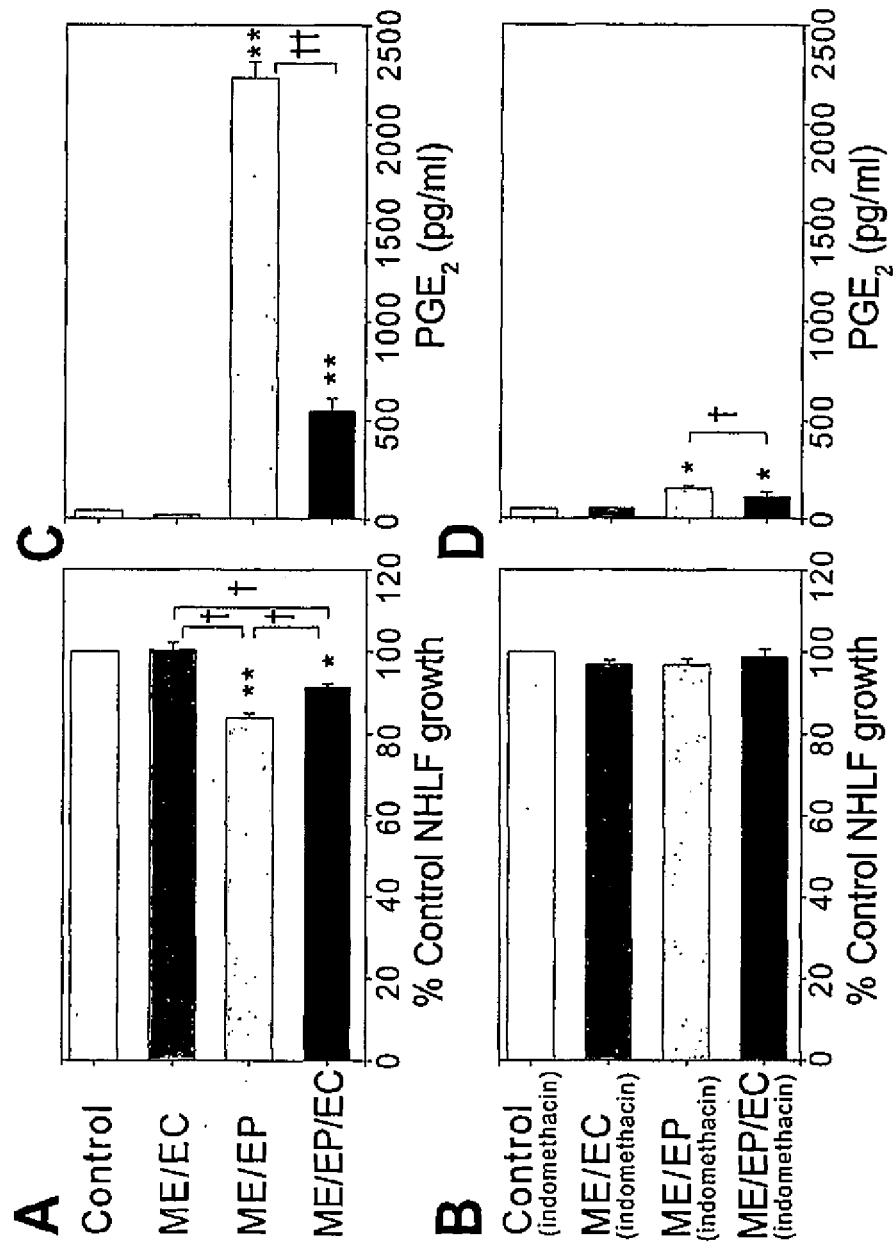
FIGS. 3A-3D are bar graphs depicting prostaglandin $E_2$ ($PGE_2$) expression in cocultures of normal human lung fibroblasts and embedded cells.

NHLF proliferation was maximally reduced when cocultured with matrices containing epithelial cells alone, modestly by embedded epithelial cells and endothelial cells, and unaffected by matrix-embedded endothelial cell cocultures. The epithelial cell effect was dependent upon prostaglandin production. Five µM of indomethacin aborted fibroblast growth inhibition (FIG. 3A-B) and production of $PGE_2$, a potent inhibitor of fibroblast proliferation, inversely correlated with NHLF growth in our coculture system ($R^2$=0.95, FIG. 3C). $PGE_2$ levels were highest (2,231.7±81.1 pg/ml) in NHLF cocultured with matrix-embedded epithelial cells, rising more than 50 fold above that seen with fibroblasts alone (40.2±2.0 pg/ml). In contrast, matrix-embedded endothelial cells reduced $PGE_2$ levels two fold (20.4±1.8 pg/ml) when alone, and limited the epithelial cells increase four fold (549.2±60.7 pg/ml). Indomethacin significantly diminished $PGE_2$ production in both NHLF cultures with embedded epithelial cells or epithelial cells and endothelial cells combined (FIG. 3D).

The secretion of mediators of vascular and bronchial biology may attain different local levels and act differently when both endothelial cells and epithelial cells are present together rather than alone. $PGE_2$ for example is a potent bronchodilator that stabilizes extracellular matrix in the airway and inhibits fibroblast proliferation. Yet, this same molecule also induces vascular permeability and edema. The influence of $PGE_2$ on bronchial injury might therefore well be appreciated differentially by epithelial cells or endothelial cells alone, or the two cells together. Indeed, embedded epithelial cells inhibition of NHLF growth correlated with production of PGE$_2$ and both were reversed by the cyclooxygenase 1 and 2 inhibitor indomethacin.

EXAMPLE 3

Tube Formation Inhibited by Matrix-Embedded Cells

The effect of matrix-embedded cells on angiogenesis in vitro was examined by tube formation of human umbilical vein endothelial cells (HUVEC) cultured with conditioned medium (CM). This process involved migration, invasion, and differentiation of HUVEC in the formation of the tubular network. A CAS™ FIT tube formation kit (Trevigen) was used. Reduced growth factor basement membrane extract purified from Engelbreth-Holm-Swarm (EHS) tumor was pipetted into wells of a 48-well plate (100 μl/well) and incubated at 37° C. for 1 hours to allow the extract to solidify. HUVEC were plated at a density of $2 \times 10^4$ cells/well and incubated at 37° C. for 8 hours with either BEGM:EGM-2 (1:1) medium unconditioned (incubated at 37° C. without cells for 48 h) or conditioned for 48 hours from matrices engrafted with endothelial cells, epithelial cells, or epithelial cells/endothelial cells.

Figure 7:
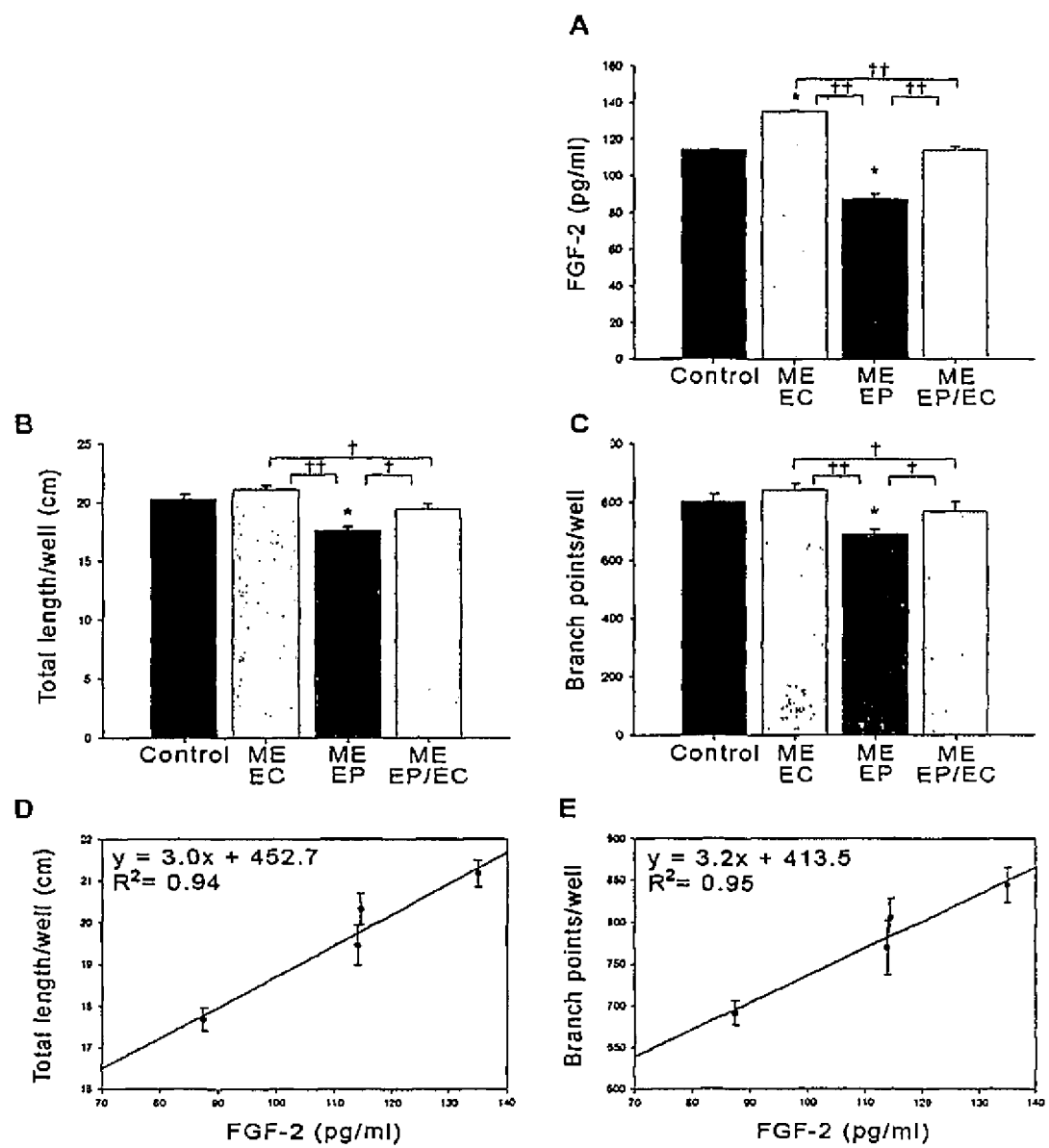
FIGS. 7A-7E are bar and line graphs depicting inhibition of tube formation by conditioned medium (CM) from matrix-embedded epithelial cells and the corresponding reduced production of fibroblast growth factor (FGF)-2.

Eight hours after seeding, images of tube formation were taken at ×40 on an inverted microscope (Nikon Diaphot) and camera (Nikon D50). Photomicrographs depicting tube formation of HUVEC under defined conditioned media were taken. Images from a total of four microscopic fields per well were analyzed using Adobe Photoshop CS3 software. The branch points of the formed tubes were counted and the length of the tube network was measured for each image and the total number of branch points and total length of the network from the four images per well were calculated. Medium from each coculture was collected and analyzed. FGF-2 (Invitrogen) levels were measured using a commercially available ELISA kit according to the manufacturer's instructions. Expression levels of FGF-2, shown in FIG. 7A, correlated with total length of tube network, shown in FIG. 7B, and total number of branch points from four microscopic fields per well, as shown in FIG. 7C (n=4–5,*p<0.01 vs. control; †p<0.05, ††p<0.001 vs. compared condition). Graphs depicting the correlation of tube length and branch point numbers with FGF-2 production by embedded cells are shown in FIG. 7D-E ($R^2$=0.95). Tube formation and FGF levels were highest with embedded endothelial cells, lowest with embedded epithelial cells, and together the cells matched acellular controls. (FIG. 7A-C).

FGF-2, like PGE$_2$, has potentially competing organ-specific functions. This growth factor is a potent vascular endothelial mitogen and angiogenic factor, but also stimulates bronchial smooth muscle cell proliferation and airway inflammation. It is therefore fascinating that while matrix-embedded epithelial cells produce the lowest amount of FGF-2 and reduce tube formation in vitro and mesenchymal vascularization in vivo, the reverse is true for endothelial cells. Matrix-embedded endothelial cells modestly enhance tube formation and branching in vitro in concert with elevated FGF-2 (FIG. 7D) and stimulate neovascularization to a small degree after airway injury. A more balanced effect is seen when the two cells are together. Vascular density is restored to control states in vivo, and branching and tube formation are restored to control levels in vitro.

What we claim is:

1. A method of effecting localized repair of an injury to a multilaminate tubular airway structure, said method comprising the step of:
   administering a composition comprising endothelial cells and epithelial cells wherein the composition, when administered to a non-luminal surface of an injured tubular airway structure, promotes vascular functionality in the vicinity of the injury while simultaneously promoting epithelial functionality within the luminal epithelium of the tubular airway structure in the vicinity of the injury.

2. The method of claim 1 wherein the composition promotes vascular functionality within the vasa vasorum in the vicinity of the injury.

3. The method of claim 1 wherein the cells are autogenic, allogenic, or xenogenic.

4. The method of claim 1 wherein the composition further comprises a biocompatible matrix which is biodegradable.

5. The method of claim 4 wherein the biocompatible matrix is a flexible planar material or a flowable composition.

6. The method of claim 5 wherein the flexible planar material is a solid polymeric support or a fibrous structure.

7. The method of claim 5 wherein the flowable composition comprises particles, beads, gels, foams, suspensions or microcapsules or combinations of any one of the foregoing.

8. The method of claim 4 wherein the biocompatible matrix is formed of a material selected from the group consisting of polyhydroxy acids, polyorthoesters, polyanhydrides, proteins, polysaccharides, polyphosphazenes and combinations of any one of the foregoing.

9. The method of claim 4 wherein the biocompatible matrix is formed of a material selected from the group consisting of ethylene vinyl acetate, polyvinyl alcohol, silicone, polyurethane, non-biodegradable polyesters, polyethyleneoxide-polypropyleneoxide, tetrafluoroethylene and combinations of any one of the foregoing.

* * * * *